United States Patent [19]

Walker et al.

[11] Patent Number: 4,781,703

[45] Date of Patent: Nov. 1, 1988

[54] CATHETER ASSEMBLY

[75] Inventors: Jack M. Walker, Portola Valley; Dwayne E. Hardy, San Mateo, both of Calif.

[73] Assignee: Menlo Care, Inc., Menlo Park, Calif.

[21] Appl. No.: 788,461

[22] Filed: Oct. 17, 1985

[51] Int. Cl.⁴ ............................................. A61M 25/00
[52] U.S. Cl. ..................................... 604/264; 604/283
[58] Field of Search ......................... 604/160, 164–170, 604/265, 266, 280, 281, 158–170, 283, 264; 128/341, 343, 768

[56] References Cited

U.S. PATENT DOCUMENTS

| | | | |
|---|---|---|---|
| 3,030,953 | 4/1962 | Koehn | 604/166 |
| 3,094,122 | 6/1963 | Gauthier et al. | 604/164 |
| 3,612,050 | 10/1971 | Sheridan | 604/166 |
| 3,633,579 | 1/1972 | Alley et al. | 604/164 |
| 3,720,210 | 3/1973 | Diettrich | 604/164 |
| 3,822,238 | 7/1974 | Blair et al. | 528/71 |
| 3,861,396 | 1/1975 | Vaillancourt et al. | 604/265 |
| 3,975,350 | 8/1976 | Hudgin et al. | 524/108 |
| 4,156,066 | 5/1979 | Gould | 528/73 |
| 4,156,067 | 5/1979 | Gould | 528/73 |
| 4,183,884 | 1/1980 | Wichterle et al. | 264/49 |
| 4,255,550 | 3/1981 | Gould | 128/155 |
| 4,381,008 | 4/1983 | Thomas et al. | |
| 4,408,023 | 10/1983 | Gould et al. | 525/454 |
| 4,411,655 | 10/1983 | Schreck | |
| 4,424,305 | 1/1984 | Gould et al. | 525/127 |
| 4,434,797 | 3/1984 | Silanoer | |
| 4,439,554 | 3/1984 | Argentar | 528/112 |
| 4,439,558 | 3/1984 | Tamosauskas et al. | 524/57 |
| 4,439,583 | 3/1984 | Gould et al. | 525/127 |
| 4,439,584 | 3/1984 | Gould et al. | 525/127 |
| 4,449,693 | 5/1984 | Gereg | 604/283 |
| 4,480,642 | 11/1984 | Stoy et al. | |
| 4,511,163 | 4/1985 | Harriss et al. | 604/283 |
| 4,526,579 | 7/1985 | Ainpour | 604/266 |
| 4,610,671 | 9/1986 | Luther | 604/168 |

FOREIGN PATENT DOCUMENTS

| | | |
|---|---|---|
| 0001106 | 5/1978 | European Pat. Off. |
| 0142222 | 8/1984 | European Pat. Off. |
| 1333898 | 1/1979 | German Democratic Rep. |
| 2065479 | 7/1981 | United Kingdom ................ 604/167 |

Primary Examiner—Stephen C. Pellegrino
Attorney, Agent, or Firm—Fliesler, Dubb, Meyer & Lovejoy

[57] ABSTRACT

A catheter assembly comprises a cannula having proximal and distal end portions and a longitudinal duct having an initial inner cross-section. The duct increases in cross-section when at least a part of the distal end portion of the cannula is inserted into a body of a living subject and maintained in contact with the body, and/or when the duct is contacted by an aqueous liquid, for a period of time sufficient for an enlarged duct cross-section to form. A hub has a passageway from a first to a second end thereof. The passageway has a cross-sectional area throughout at least substantially equal to 125% of the initial inner cross-section of the duct. A proximal end portion of the cannula is attached to the first end of the hub with a passageway through the hub in flow communication with the duct in the proximal end portion of the cannula. The attaching is such that the cross-section of the duct adjacent the proximal end portion, following formation of the enlarged duct cross-section, is throughout at least substantially equal to the cross-sectional area of the passageway. Increased flow is provided through the hub whereby advantage can be taken of the expansion of the duct.

32 Claims, 5 Drawing Sheets

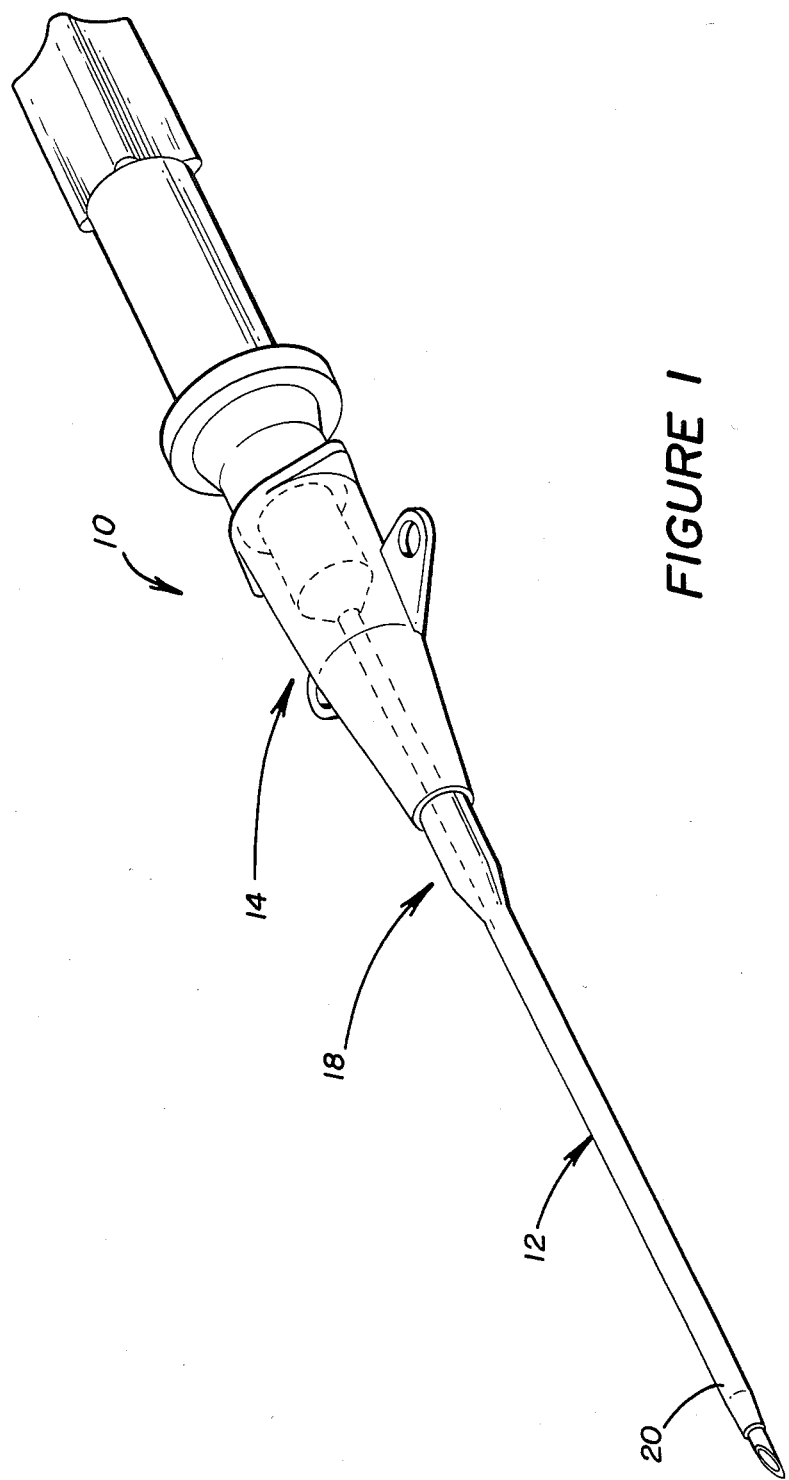

FIGURE 2A
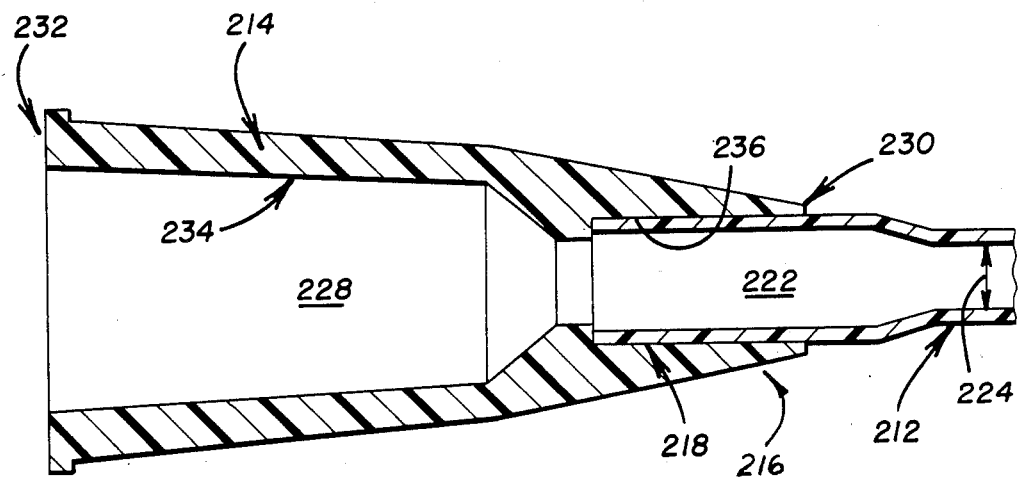
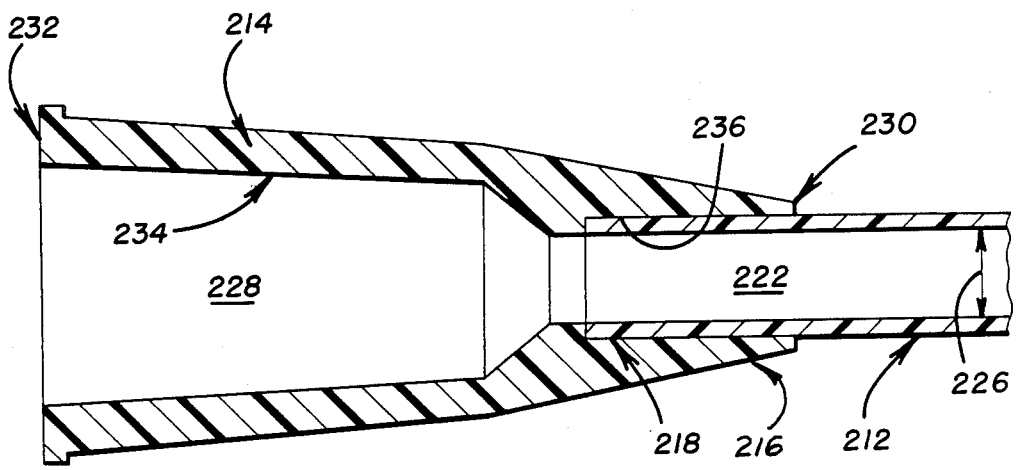
FIGURE 2B

CATHETER ASSEMBLY

TECHNICAL FIELD

The invention relates to a catheter assembly useful as a body implant for introduction of nutrients and/or medication to and/or extraction of fluids from an animal species. More particularly, the invention relates to a catheter assembly which utilizes a unique hub in combination with a cannula formulated of a material which expands whereby increased fluid flow is attained.

BACKGROUND

A number of catheter assemblies are known which utilize a relatively long flexible hollow plastic cannula for insertion into the vein of a patient for the infusion of intravenous fluids including nutrients and/or medication. Generally, one end of the cannula is attached to the hub and a steel needle which is sized to fit within the duct of the cannula is inserted into the hub from the side opposite the attachment of the cannula sufficiently so that the steel needle exits the cannula at its distal end. The needle is then inserted into the vein of a patient after which it is removed from the cannula and the hub, leaving the cannula behind with its distal end in the vein. An intravenous feeding and/or medication tube is then attached to the hub whereby flow can take place through the hub and the cannula and into the vein.

Catheter assemblies are also used for other purposes, for example, for endotracheal tubes, and the like. Also, the cannula of such assemblies can be inserted by over the needle and through the needle techniques and, in the case of endotracheal tubes or the like, without the use of a needle.

The cannulae of the prior art have generally been made of a rigid material which does not change the cross-sectional area of the duct of the cannula after insertion into a vein. More recently, as set forth in commonly assigned co-pending U.S. patent application Ser. No. 780,543 filed Sept. 26, 1985, materials have been developed which can be formulated into cannulae and which, while they are rigid enough to retain their shape during insertion, also, have the property of swelling to form an enlarged duct cross-section, due to water pickup. Also, recent publications discuss cannulae which, on being raised to a temperature approaching body temperature undergo a shape change motivated by plastic memory, to form somewhat shorter, larger duct cross-section cannulae.

If such increasing duct cross-section cannulae as are discussed above are attached to the conventional hubs of the prior art the full effect of the increased duct cross-section, in flow rate, cannot be realized because prior art hubs are such that flow will be limited either because of the size of the passageway through the hubs or because the hubs hold the cannulae in such a manner that instead of the cannulae proximal ends being held so that the duct cross-section can increase, the cannulae are externally restrained whereby the duct cross-section is forced to decrease.

The present invention is directed to overcoming one or more of the problems as set forth above.

DISCLOSURE OF THE INVENTION

One aspect of the present invention is a catheter assembly comprising a cannula having a proximal end portion, a distal end portion and a longitudinal duct therethrough, the cannula being of a material such that an inner cross-section of the duct increases to form an increased duct cross-section when at least a part of the distal end portion is inserted into a body of a living subject and maintained in contact with the body, and/or when the duct is contacted by an aqueous liquid, for a period of time sufficient for the enlarged duct cross-section to form. The catheter assembly further includes a hub having a passageway therethrough from a first to a second end thereof, the passageway having a cross-sectional area throughout at least substantially equal to the enlarged duct cross-section. Attaching means are provided for attaching the proximal end portion of the cannula to the first end of the hub with the passageway through the hub in flow communication with the duct in the proximal end portion of the cannula, the attaching being in a manner such that the cross-sectional area of the duct adjacent the proximal end portion, following formation of the enlarged duct cross-section, is throughout at least substantially equal to the enlarged duct cross-section along the remainder of the cannula.

Another aspect of the present invention is a catheter assembly comprising a cannula having proximal and distal end portions and a longitudinal duct therethrough, the cannula being of a material such that an inner cross-section of the duct increases to form an enlarged duct cross-section when at least a part of the distal end portion is inserted into a body of a living subject and maintained there, and/or when the duct is contacted by an aqueous liquid, for a period of time sufficient for the enlarged cross-section to form. The catheter assembly further comprises a hub having a passageway therethrough from a first to a second end thereof, the passageway having a cross-sectional area throughout at least substantially equal to the enlarged duct cross-section, the first end of the hub and the proximal end portion of the cannula being attached with the passageway and duct in flow communication, the attaching being in a manner such that the cross-sectional area of the duct adjacent the proximal end portion, following formation of the enlarged duct cross-section, is throughout at least substantially equal to the enlarged duct cross-section along the remainder of the cannula.

Still another aspect of the present invention is a catheter assembly comprising a cannula having a proximal end portion, a distal end portion and a longitudinal duct therethrough, the duct having an initial inner cross-section which increases to form an increased duct cross-section when at least a part of the distal end portion of the cannula is inserted into a body of a living subject and maintained in contact with the body, and/or when the duct is contacted by an aqueous liquid, for a period of time sufficient for the enlarged duct cross-section to form. The catheter assembly further includes a hub having a passageway therethrough from a first to a second end thereof, the passageway having a cross-sectional area throughout at least substantially equal to 125% of the initial inner cross-section of the duct. Attaching means are provided for attaching the proximal end portion of the cannula to the first end of the hub with the passageway through the hub in flow communication with the duct in the proximal end portion of the cannula, the attaching being in a manner such that the cross-sectional area of the duct adjacent the proximal end portion, following formation of the enlarged duct cross-section, is throughout at least substantially equal to the cross-sectional area of the passageway.

Another aspect yet of the present invention is a catheter assembly comprising a cannula having proximal and distal end portions and a longitudinal duct therethrough, the duct having an initial inner cross-section which increases to form an enlarged duct cross-section when at least a part of the distal end portion of the cannula is inserted into a body of a living subject and maintained there, and/or when the duct is contacted by an aqueous liquid, for a period of time sufficient for the enlarged cross-section to form. The catheter assembly further comprises a hub having a passageway therethrough from a first to a second end thereof, the passageway having a cross-sectional area throughout at least substantially equal to 125% of the initial inner cross-section of the duct, the first end of the hub and the proximal end portion of the cannula being attached with the passageway and duct in flow communication, the attaching being in a manner such that the cross-sectional area of the duct adjacent the proximal end portion, following formation of the enlarged duct cross-section, is throughout at least substantially equal to the cross-sectional area of the passageway.

Utilizing a catheter assembly in accordance with the present invention one can take full advantage of the enlarged duct cross-section in the cannula whereby one can utilize smaller steel needles and cannulae for insertion into the body to attain a throughput equal to that attained utilizing such relatively larger needles as are currently in use or, alternatively, one can utilize steel needles and cannulae of the size presently used and can thereby attain a much higher throughput.

BRIEF DESCRIPTION OF THE DRAWINGS

The invention will be better understood by reference to the figures of the drawings wherein like numbers denote like parts throughout and wherein:

FIG. 1 is a perspective view of a catheter assembly in accordance with an embodiment of the present invention;

FIG. 2a is a cross-sectional view of an embodiment of a hub and the preshaped proximal end portion of a cannula in accordance with an embodiment of the present invention in a non-expanded state;

FIG. 2b is a view similar to FIG. 2a but with the cannula in the expanded state;

BEST MODE FOR CARRYING OUT THE INVENTION

Figure 3A:
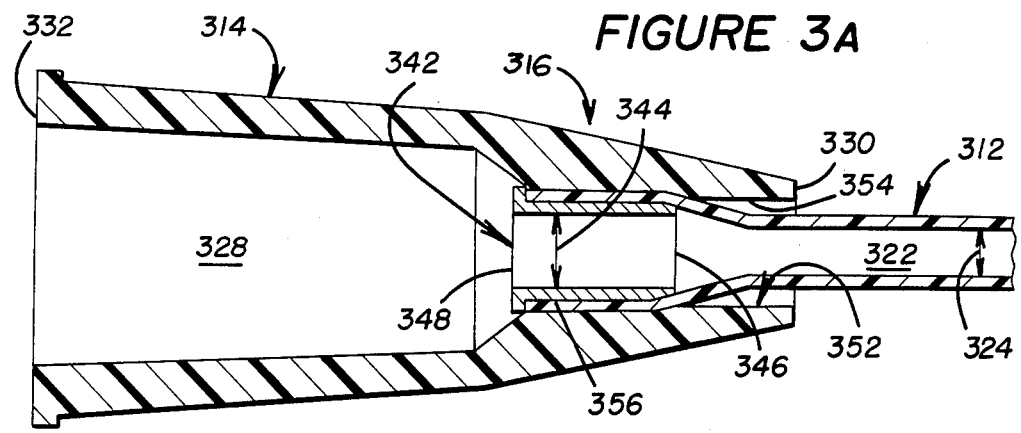
FIG. 3a is a view similar to FIG. 2a but showing an alternate embodiment of a catheter assembly in accordance with the present invention with the cannula in the non-expanded state.

In the following description corresponding parts of the structures called out are distinguished from one embodiment to another by preceeding the number of the part with the number of the Figure. Thus, for example, part 216 in FIG. 2 corresponds to part 316 in FIG. 3, part 416 in FIG. 4, part 516 in FIG. 5, and part 616 in FIG. 6. The following discussion is directed to an over the needle type of catheter assembly 10. However, while the discussion is limited in this manner such limitation is for convenience only. Thus, cannulae which are long tubes and short tubes, catheter assemblies which are inserted by other than an over the needle technique, and the like, also fall within the scope of the invention.

The invention relates to a catheter assembly 10, one embodiment of which is seen in perspective in FIG. 1. The catheter assembly 10 includes a cannula 12 along with a hub 14 and attaching means 216, 316, 416 and 516 (seen in FIGS. 2-6). The cannula 12 has a proximal end portion 18 and a distal end portion 20. A longitudinal duct 222, 322, 422, 522 and 622 (FIGS. 2-6) is defined within the cannula 12 and extends therethrough from the proximal end portion 18 to the distal end portion 20. It is essential to the practice of the present invention that the cannula 12 be formulated of a material selected such that an inner cross-sectional area (at 224, 324, 424, 524, 624) of the duct 222, 322, 422, 522, 622 increases to form an enlarged duct cross-sectional area (at 226, 326, 526, 626), generally enlarged from at least about 25% (to 125% of its initial inner cross-section) to at least about 300%, preferably from about 40% to about 300%; for over the needle cannulae the enlargement is more preferably from about 35% to about 140% and most preferably from about 40% to about 100%; when at least a part of the distal end portion 20 of the cannula 12 is inserted into a body, generally into the blood stream, of a living subject and maintained in contact with that body, and/or when the duct 222, 322, 422, 522, 622 is contacted by, e.g., filled with, an aqueous liquid, for a time sufficient for the enlarged duct cross-section (at 226, 326, 426, 526) to form.

In accordance with a preferred embodiment of the present invention the cannula comprises a multiple phase polymeric composition comprising a first phase which comprises a substantially non-hydrophilic polymeric component and a second phase which comprises a hydrophilic polymeric component. The relative amounts of these components are selected, depending on the particular polymeric materials employed, to provide a composition having the desired properties, as discussed more fully below.

Preferably the non-hydrophilic polymeric component forms a continuous phase. The hydrophilic polymeric component can form a co-continuous phase with, or a dispersed phase in, the non-hydrophilic polymer phase.

The non-hydrophilic polymeric component comprises a polymer which does not substantially absorb or attract water. Preferably, the non-hydrophilic polymer is capable of absorbing in an amount of no more than about 30%, more preferably no more than about 15%, and most preferably no more than about 10%, by weight, based on the weight of the non-hydrophilic polymer.

The non-hydrophilic polymer can be for example, a polyurethane such as an aliphatic polyurethane, a polyether polyurethane, a polyester polyurethane; an ethylene copolymer such as ethylene-vinyl acetate copolymer or ethylene-ethyl acrylate copolymer; a polyamide, in particular a polyamide of low crystallinity; an aliphatic polyester; or the like. A particularly preferred non-hydrophilic polymer is a polyurethane, especially an aliphatic polyurethane.

The hydrophilic polymer preferably is a polymer that absorbs at least about 50% water, more preferably about 100%, for example, at least about 150%, by weight based on the weight of the hydrophilic polymer. The hydrophilic polymer preferably forms a hydrogel on absorption of water.

The hydrophilic polymer is preferably polyvinyl alcohol, poly(ethylene oxide), polypropylene oxide, poly(ethylene glycol), polypropylene glycol, polytetramethylene oxide, polyvinyl pyrolidene, polyacrylamide, poly(hydroxyethyl acrylate), poly(hydroxyethyl methacrylate), or the like.

The multiple phase composition can be prepared by mixing the polymeric components or by forming a block or graft copolymer containing the polymeric components. A mixture of the components can be prepared using, for example, a two-roll mill, an internal mixer, such as a Brabender or Banbury mixer, an extruder, e.g., twin-screw extruder, or the like. Block and graft copolymers can be prepared by appropriate methods depending on the particular nature of the components used. Typical preparatory methods can be found, for example, in "Block and Graft Copolymerization", R. J. Ceresa (Zd), 1973, Vol. 1 & 2, Wiley-Interscience, N.Y. and "Block Copolymers", D. C. ALlport and W. H. Jane, 1973, Wiley, N.Y.

Generally, the ratio of non-hydrophilic polymeric component to hydrophilic polymeric component is 0.65:1 to 9:1. Preferably the ratio of the polymeric components is 1:1 to 9:1.

The polymeric components are selected to provide a multiple phase system. Generally, the polymeric components each have a molecular weight of at least about 3,000 preferably at least about 5,000 and most preferably at least about 10,000.

As stated above, the relative amounts of non-hydrophilic and hydrophilic polymeric components are selected, depending on the particular materials employed, to provide the desired properties. Due to the presence of the hydrophilic polymeric component, the composition is capable of being hydrated by the absorption of water. As water is absorbed by the composition, it may soften with a softening ratio of at least about 2:1, preferably at least 6:1, more preferably at least about 10:1, most preferably at least about 20:1, and in particular at about 40:1. The term "softening ratio" is used herein to refer to the ratio of the 2.5% Secant modulus values of the composition, in the form of a tubular article, when substantially non-hydrated, to the 2.5% Secant modulus of the composition when substantially completely hydrated. The term "substantially non-hydrated" refers to the state of the composition under conventional ambient conditions, i.e., room temperature, 50-80% relative humidity and about atmospheric pressure. The term "substantially completely hydrated" refers to the state of the composition when it is in equilibrium with an excess of water at 37° C. and ambient pressure.

The composition may swell on absorption of water with a swelling ratio of at least about 1.3:1, preferably at least about 1.7:1 and most preferably at least about 2.0:1. The term "swelling ratio" refers to the ratio of the volume of a given sample of the composition when substantially completely hydrated to its volume when substantially non-hydrated.

Preferably the composition both softens and swells when placed in the body.

When substantially completely hydrated the composition has a tensile energy to break of at least about 700 Newton-centimeters per cubic centimeter (N-cm/cm$^3$), preferably at least about 1,400 N-cm/cm$^3$ and most preferably about 1,700 N-cm/cm$^3$. The term "tensile energy to break" (TEB) is defined in ASTM-D882 as the area under the stress-strain curve or $$TEB = \int_0^{\epsilon_r} S d\epsilon$$

where S is the stress at any strain, $\epsilon_,$; and $\epsilon_r$ is the strain at rupture. The tensile energy to break provides an indication of the toughness of the hydrated composition and its ability to withstand the conditions it will be subjected to in use.

It will be readily appreciated that when a tubular product such as a cannula is withdrawn from the body it is extremely important that it does not tear or break leaving pieces remaining inside the body. Neither tensile strength nor elongation to break are good indicators of toughness. Brittle materials and notch sensitive materials can have tensile strengths. Extremely weak materials can have high elongation but not the strength to survive extraction. TEB is a measure of the energy required to break and is a combination of these two important criteria.

The ultimate elongation of the multiple phase composition should be at least about 10%, preferably at least about 25% and most preferably at least about 50%.

The composition when substantially completely hydrated has a 2.5% Secant modulus of less than about 7,000 Newtons/square centimeter (N/cm$^2$), preferably less than about 3,500 N/cm$^2$ and most preferably less than about 2,000 N/cm$^2$. When substantially completely hydrated the 2.5% Secant modulus can be as low as about 30 N/cm$^2$ but preferably above about 60 N/cm$^2$ and most preferably above about 120 N/cm$^2$.

Typically the 2.5% Secant modulus of the composition when substantially non-hydrated is at least about 20,000 N/cm$^2$ when used as over the needle catheter in accordance with the present invention. Preferably the 2.5% Secant modulus of the composition is at least about 28,000 N/cm$^2$.

The composition may be crosslinked if desired. Crosslinking of the composition gives the polymeric composition strength above the melting or softening points of the polymeric components permitting sterilization of a device utilizing the composition at above that temperature. This is particularly advantageous if the polymeric component of the continuous phase has a relatively low melting or softening point. Crosslinking of the composition may also be used to adjust the 2.5% Secant modulus of the composition to bring it to the desired value for the proposed use of the composition. When the composition comprises a physical mixture of the non-hydrophilic and hydrophilic components, crosslinking of the mixture can control the tendency of the hydrophilic component to leach out of the composition when it is in extended contact with water or body fluids. Crosslinking may also improve the toughness (TEB) of the composition in the hydrated state.

Crosslinking of the composition can be effected by use of an appropriate crosslinking agent or by irradiation, preferably in the presence of a crosslinking promoter, such as triallyl isocyanurate, or the like. In a preferred embodiment the composition is crosslinked by high energy radiation from an electron accelerator. The amount of irradiation should be in the range of about 0.5 to about 30 Megarads (Mrads) preferably about 0.5 to about 15 Mrads and most preferably about 0.5 to about 10 Mrads.

Either or both components of the composition may contain additional ingredients such as stabilizers, antioxidants, radiopacifiers, medicaments, fillers or the like. For certain applications it may be advantageous to incorporate a water soluble or water dispersible medicament which can leach from the composition of the cannula when it contacts body fluids. Such medicaments include anti-thrombogenic agents, antibiotics, anti-viral agents, anticoagulants, anti-inflammatory agents or the like.

The cannula should not swell or soften appreciably during the time it is being inserted in a vein or the like. It has been found that the time for the cannula to swell to 50% of its fully swollen volume should be at least about 15 seconds, preferably at least about 60 seconds.

An alternative material which may be utilized as the cannula material is a thermoplastic material with shape-memory properties. Such polymeric compounds are described, for example, in the following articles: Softenable, Shape-Memory Thermoplastics For Biomedical Use, Robert S. Ward, MD7D, August 1985; and Thromboresistant, Radiopaque, Softenable Thermoplastic Catheter Compound With Shape-Memory Properties, R. S. Ward, K. A. White, J. S. Riffle, Second World Congress On Biomaterials, 10th Annual Meeting Of The Society For Biomaterials, Washington, D.C., Apr. 27-May 1, 1984. The aforementioned thermoplastic materials comprise a base polymer that is a block or segmented co-polymer thermoplastic with at least one block type which has an abrupt glass transition temperature ($T_g$) at or greater than room temperature, but less than approximately body temperature. The remainder of the base polymer contains hard blocks whose dominant thermal transition is substantially greater than body temperature. The cannulae are originally made with their eventually desired expanded internal diameter and then are heated above the glass transition ($T_g$), drawn out to form longer and thinner cannulae and held in this state until cooled below the ($T_g$) Once the longer and thinner cannulae have warmed to a temperature that is greater than room temperature but less than approximately body temperature, i.e., once the cannulae have reached the glass transition temperature, $T_g$, the shape-memory properties operate and the cannulae increase in internal and external diameter while shrinking in length.

FIGS. 2a and 2b illustrate an embodiment of the invention wherein the hub 214 has a passageway 228 therethrough from a first end 230 to a second end 232 thereof. The passageway 228 has an inner surface 234 selected so that the passageway 228 has a cross-sectional area throughout which is at least substantially equal to 125% of the initial duct cross-section 224 and is preferably at least substantially equal to the enlarged duct cross-section 226 (FIG. 2b). In the embodiment of FIGS. 2a and 2b this is accomplished by providing a counterbore 236 which extends inwardly from the first end 230 of the hub 214 coaxially with the passageway 228 and is of a sufficient size so that when the cannula 212 swells its cross-section in the counterbore 236 is at least equal to 125% of the initial duct cross-section 224 and is preferably at least equal to the enlarged duct cross-section 226. In such a situation the proximal end portion 218 of the cannula 212 is preshaped or preformed, as by being pre-expanded, pre-molded or the like, and has substantially the aforementioned enlarged duct cross-section 226 and the proximal portion 218 is positioned within the passageway 228 at the first end 230 of the hub 214. The attaching means 216, in the embodiment of FIGS. 2a and 2b includes the counterbore 236 of the passageway 228 which extends inwardly from the first end 230 of the hub 214. The counterbore 236 is bonded to an outer surface 240 of the proximal end portion 218 of the cannula 212 by being insert injection molded, by solvent welding, by RF welding, using a bonding composition, or by any other appropriate technique. In the particular embodiment illustrated in FIG. 2a the proximal end portion 18 of the cannula 212 has been preshaped, e.g., thermally, until it has a duct cross-section that equals or exceeds the enlarged cross-section 226 while the majority of the cannula 212 has not yet been expanded.

Figure 3B:
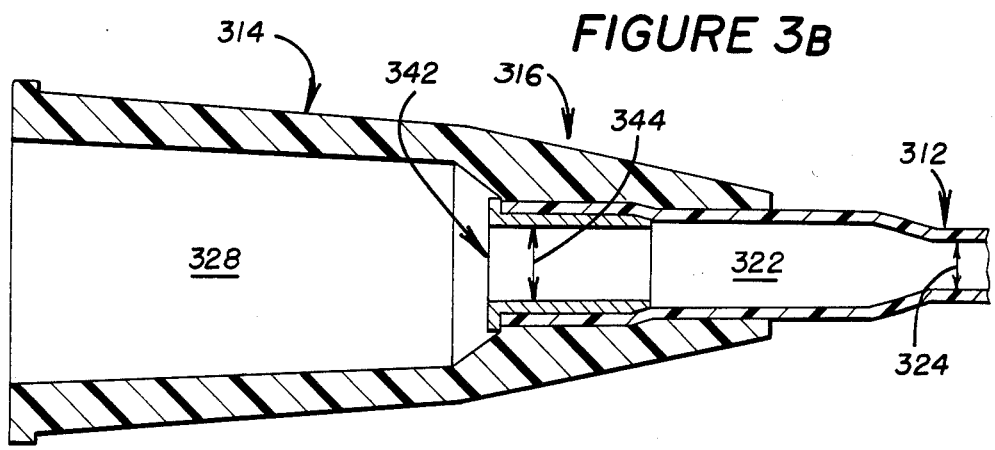
FIG. 3b is a view similar to FIG. 3a but with the cannula proximal end portion preshaped.
Figure 3C:
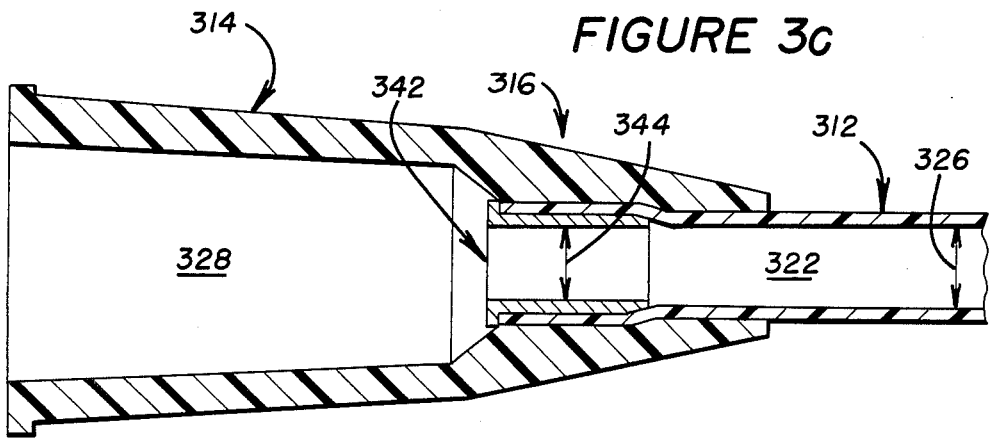
FIG. 3c is a view similar to FIG. 3a but with the cannula in the expanded state.

Adverting now to FIGS. 3a, 3b and 3c, there is illustrated an embodiment of the present invention which includes the use of a hub insert 342. In the embodiment of FIG. 3a the hub insert 342 has an opening 344 therethrough from a first end 346 to a second end 348 thereof. The opening 344 has an inner cross-section which is throughout at least substantially equal to 125% of the initial duct cross-section 324 and is preferably at least substantially equal to the enlarged duct cross-section 326 (FIG. 3c). A part 352 of the passageway 328 in the hub 314 adjacent the first end 330 of the hub 314 has an inner surface which is geometrically similar to and positioned about an outer surface 356 of the hub insert 342. The part 352 of the passageway 328 and the outer surface 356 of the hub insert 342 are adapted to hold the proximal end portion 318 of the cannula 312 impressed therebetween. If desired, a bonding composition can be attached between the hub insert 342 and the duct 322 and/or between the part 352 of the passageway 328 and the outer surface of the proximal end portion 318 of the cannula 312.

FIG. 3a illustrates an embodiment wherein the cannula 312 is in the non-expanded state and has not yet expanded through contact with a liquid or through being heated to between room temperature and body temperature. The proximal end portion 318 of the cannula 312 has been forced over the hub insert 342, thus preshaping or preforming it only adjacent the hub insert 342. Alternatively, the proximal end portion 318 may be thermally or otherwise preshaped or preformed. FIG. 3b is similar to FIG. 3a but illustrates the cannula 312 as being preshaped interiorly and exteriorly of the hub 314 to have a duct cross-section that equals or exceeds the enlarged duct cross-section 326. FIG. 3c illustrates the embodiment wherein the cannula 312 is in the expanded state.

Figure 4:
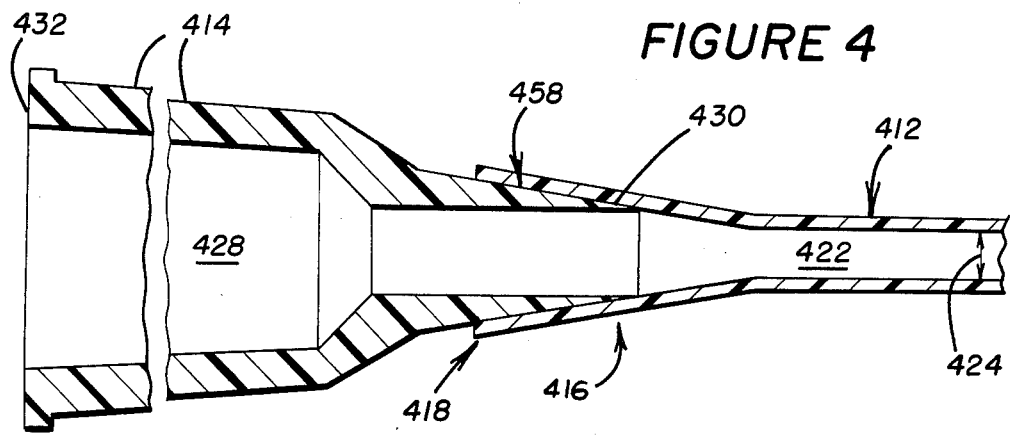
FIG. 4 illustrates, in a view similar to FIG. 2a, another alternate embodiment in accordance with the present invention.

FIG. 4 illustrates an embodiment of the present invention wherein the attaching means 416 includes a tapered outer surface 458 on the first end 430 of the hub 414 which tapers to a smallest dimension towards the cannula 412 and which holds the proximal end portion 418 of the cannula 412 thereabout in interference fit. If desired, a bonding compound can be placed between the inner surface of the cannula 412 and the tapered outer surface 458 on the first end 430 of the hub 414 or bonding may be accomplished by insert injection molding of the parts, by solvent or RF welding, by using a bonding composition or by another appropriate technique. FIG. 4 shows the cannula 412 in its non-expanded state. The cross-section of the passageway 428 is throughout at least 125% of the initial duct cross-section 424. Preferably in its expanded state the internal cross-section of the duct 422 expands to a size less than or equal to the smallest cross-section of the passageway 428.

Figure 5A:
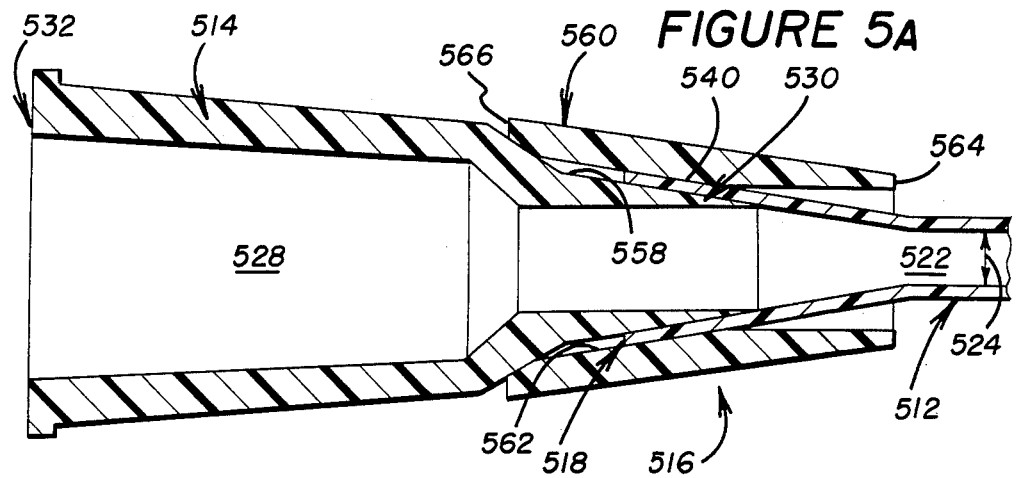
FIG. 5a illustrates another embodiment yet of the present invention with the cannula in a non-expanded state.
Figure 5B:
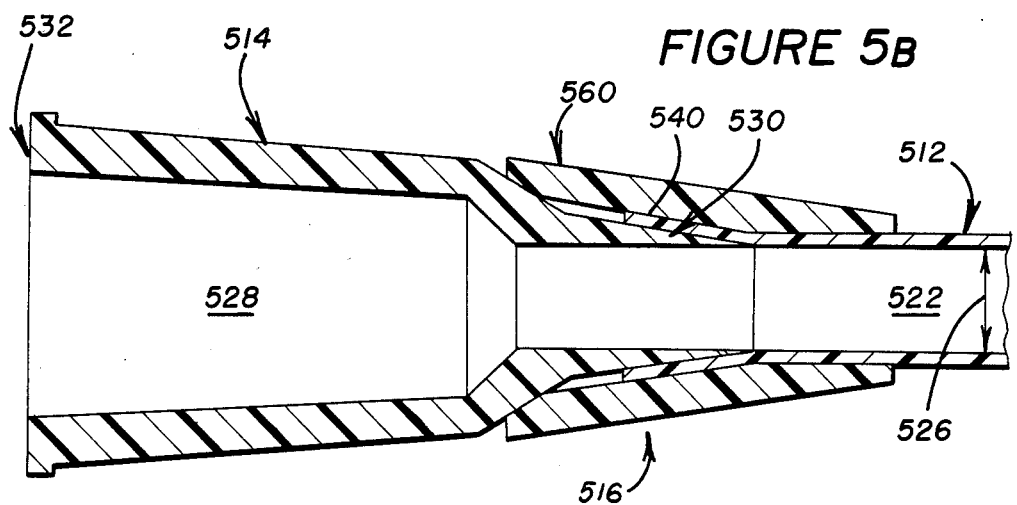
FIG. 5b illustrates a view similar to FIG. 5a but with the cannula in its expanded state.
Figure 5C:
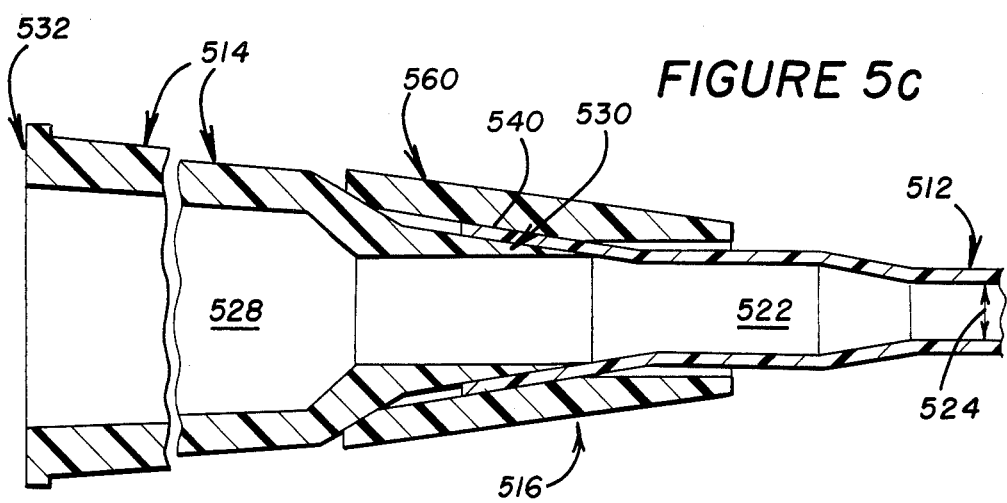
FIG. 5c illustrates an alternate embodiment of the present invention similar to that of FIG. 5a but wherein the cannula has been preshaped at its proximal end portion.

FIGS. 5a, 5b and 5c illustrate embodiments closely related to the embodiment of FIG. 4. These embodiments differ from the embodiment of FIG. 4 in that the attaching means 516 further includes an outer member 560 having an opening 562 therethrough from a first end 564 to a second end 566 thereof. The opening 562 is generally geometrically similar to the tapered outer surface 558 of the first end 530 of the hub 514. The outer member 560 is positioned about the tapered outer surface 558 of the first end 530 of the hub 514 with the inner surface of the opening 562 bearing against the outer surface 540 of the proximal end portion 518 of the cannula 512. The outer member 560 may engage with the hub 514 as by screwing thereon, by solvent or OF welding, by using a bonding composition or by another appropriate technique. FIG. 5a shows the cannula 512 in its non-expanded state while FIG. 5b shows the cannula 512 in its expanded state. FIG. 5c illustrates the embodiment wherein the cannula 512 is in the non-expanded state but wherein the proximal end portion 518 of the cannula 512 has been preshaped so that its duct cross-section equals or exceeds the enlarged duct cross-section 526.

It will be noted that throughout the various above described embodiments of the present invention the attaching means 216, 316, 416, 516 serves for attaching the proximal end portion 218, 318, 418, 518 of the cannula 212, 312, 412, 512 to the first end 230, 330, 430, 530 of the hub 214, 314, 414, 514 with the passageway 228, 328, 428, 528 through the hub 214, 314, 414, 514 in flow communication with the duct 222, 322, 422, 522 in the proximal end portion 218, 318, 418, 518 of the cannula 212, 312, 412, 512. Also, the attaching is in a manner such that the cross-section of the duct 222, 322, 422, 522 adjacent the proximal end portion 218, 318, 418, 518 thereof is throughout at least substantially equal to the enlarged duct cross-section 226, 326, 526 along the remainder of the cannula 212, 312, 412, 512 that results from exposure to body temperature and/or fluids.

Having the proximal end portion 218, 318, 418, 518, of the duct 222, 322, 422, 522, of the cannula 212, 312, 412, 512 be preshaped to be of larger cross-section than is the remainder of the cannula 212, 312, 412, 512 before insertion into a body is useful in that it allows the user of the catheter assembly 10 to visually observe just how big a cannula 212, 312, 412, 512 will be formed once expansion has taken place (i.e., upon insertion into the body). Furthermore, in certain instances it is easier to utilize the attaching means 216, 316, 416, 516 if the proximal end portion 218, 318, 418, 518 of the duct 222, 322, 422, 522 of the cannula 212, 312, 412, 512 is of larger cross-section than is the remainder of the cannula 212, 312, 412, 512.

Figure 6A:
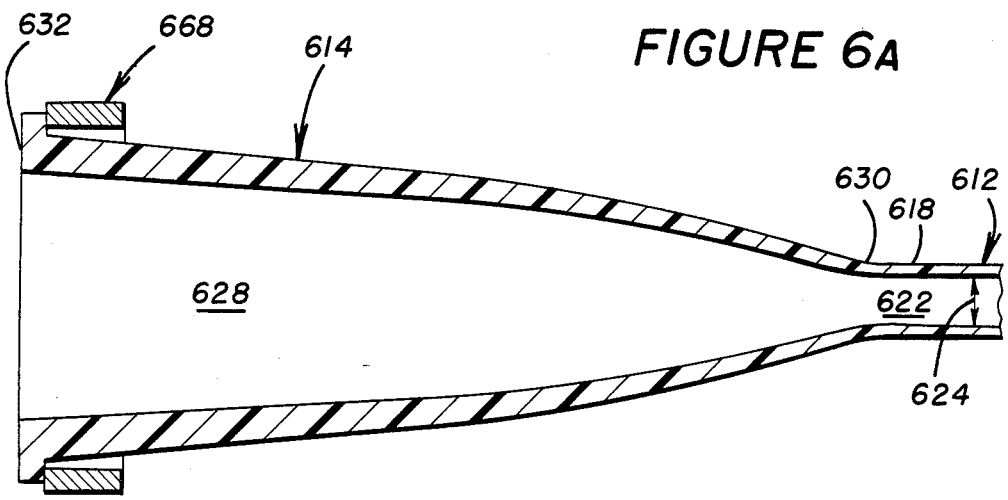
FIG. 6a illustrates yet another embodiment of the present invention wherein the hub and cannula are of integral construction in the non-expanded state.
Figure 6B:
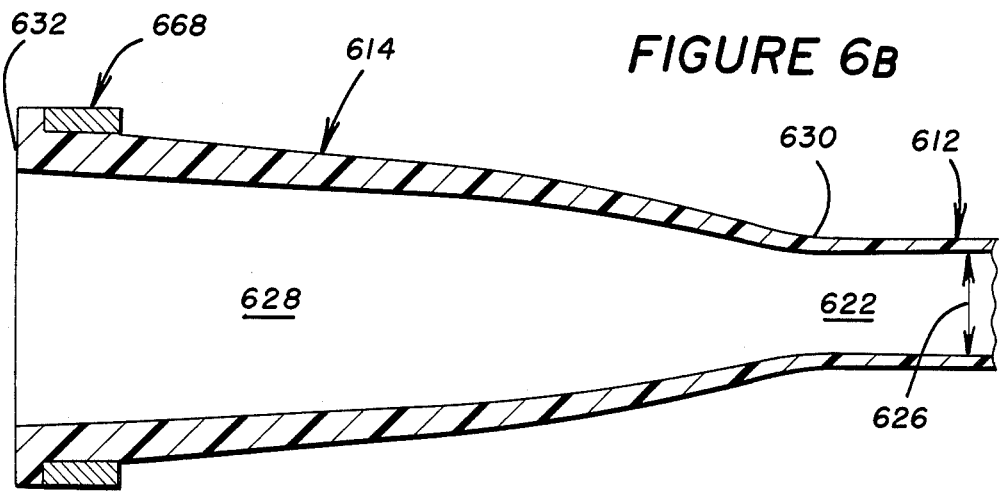
FIG. 6b illustrates the embodiment of FIG. 6a with the hub and cannula in the expanded state.

FIGS. 6a and 6b illustrate an embodiment of the invention wherein the hub 614 and the cannula 612 are of integral construction with the first end 630 of the hub 614 integral with the proximal end portion 618 of the cannula 612 and with the duct 622 being a continuation of the passageway 628. In such a structure the hub 614, like the cannula 612, is formulated of a material such that an inner cross-section of the passageway 628 increases when at least a part of the distal end portion 20 of the cannula 612 is inserted into a body of a living subject and maintained in the body and/or when the passageway 628 or the duct 622 is contacted by an aqueous liquid, for a period of time sufficient for the enlarged duct cross-section to form. Accordingly, when the cannula 612 increases in cross-section so does the hub 614. The area which would correspond to the first end 630 of the hub 614, if the hub 614 was not integrally joined to the cannula 12, generally has a relatively thin wall so that it can increase in cross-section along with the area which would correspond to the proximal end portion 618 of the cannula 612. The second end 632 of the hub 614 generally has a thicker wall than the area which would correspond to the first end 630 so that the passageway 628, adjacent the second end 632 of the hub 614, can retain connection about an input tube (not shown) from a liquid source. A retaining ring 668 positioned about the second end 632 of the hub 614 can serve as means for preventing radial expansion thereof thus aiding in retention of connection about an input or output tube.

INDUSTRIAL APPLICABILITY

In accordance with the present invention a catheter assembly 10 is set forth which is useful for introduction of medication and nutrients to and/or extraction of body fluids from a patient.

Other aspects, objectives and advantages of the present invention can be obtained from a study of the drawings, the disclosure and the appended claims.

We claim:

1. A catheter assembly, comprising:

a unitary cannula having a proximal end portion, a distal end portion, and a longitudinal duct therethrough from the proximal end portion to the distal end portion, the cannula being of a polymeric material selected such and having the intrinsic property that an inner cross-section of the duct increases to form an enlarged duct cross-section when at least a part of the distal end portion of the cannula is inserted into a body of a living subject and maintained in said body, and/or when the duct is contacted by an aqueous liquid, for a period of time sufficient for the enlarged duct cross-section to form;

a hub having a passageway therethrough from a first to a second end thereof, said passageway having a cross-sectional area throughout at least substantially equal to the enlarged duct cross-section; and attaching means for attaching said proximal end portion of said cannula to said first end of said hub with said passageway through said hub in flow communications with said duct in said proximal end portion of said cannula, said attaching being in a manner such that the cross-sectional area of the duct adjacent the proximal end portion, following formation of the enlarged duct cross-section, is throughout at least substantially equal to the enlarged duct cross-section along the remainder of the cannula.

2. A catheter assembly as set forth in claim 1, wherein the increase in the duct cross-section is at least about 25%.

3. A catheter assembly as set forth in claim 1, wherein the proximal end portion of the cannula has the enlarged duct cross-section preformed thereat and the cannula is positioned within the passageway at the first end of the hub and wherein the attaching means includes a part of the passageway extending inwardly from the first end of the hub having an inner surface bonded to an outer surface of the proximal end portion of the cannula having the enlarged duct cross-section.

4. A catheter assembly as set forth in claim 1, wherein the attaching means includes (1) a hub insert having an opening therethrough from a first end to a second end thereof, said opening having an inner cross-sectional area which is throughout at least substantially equal to the enlarged duct cross-section and (2) a part of the passageway adjacent the first end of the hub, the part of the passageway having an inner surface geometrically similar to and positioned about an outer surface of the hub insert, the part of the passageway and the outer surface of the hub insert being adapted to hold the proximal end portion of the cannula in pressed or bonded fit therebetween.

5. A catheter assembly as set forth in claim 1, wherein said attaching means includes a tapered outer surface on said first end of said hub tapering to a smallest dimension towards said cannula and holding said proximal end portion of said cannula thereabout.

6. A catheter assembly as set forth in claim 5, including means bonding said tapered outer surface to said duct at said proximal end portion of said cannula.

7. A catheter assembly as set forth in claim 5, wherein said attaching means further includes an outer member having an opening therethrough from a first end to a second end thereof, said opening having an inner surface which is generally geometrically similar to said tapered outer surface of said first end of said hub, said outer member being positioned about said tapered outer surface of said first end of said hub with said inner surface thereof bearing against said outer surface of said proximal end portion of said cannula.

8. A catheter assembly as set forth in claim 1, wherein said proximal end portion of said duct of said cannula is preformed to be of larger cross-section than is the remainder of said cannula.

9. A catheter assembly as set forth in claim 1, wherein said material of said cannula comprises:
(a) a first phase which comprises a substantially non-hydrophilic polymeric component; and
(b) a second phase which comprises a hydrophilic polymeric component;
said material (i) being capable of absorbing water to an extent that it softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant modulus of less than about 7,000 N/cm$^2$.

10. A catheter assembly as set forth in claim 1, wherein said material of said cannula comprises a thermoplastic compound with shape-memory properties and with a glass transition temperature of greater than room temperature but less than about body temperature.

11. A catheter assembly as set forth in claim 1, wherein said cannula is of a plastic material.

12. A catheter assembly as set forth in claim 1, wherein said cannula has an unbroken wall.

13. A catheter assembly, comprising:
a unitary cannula having a proximal end portion, a distal end portion, and a longitudinal duct therethrough from the proximal end portion to the distal end portion, the cannula being of a polymeric material selected such and having the intrinsic property that an inner cross-section of the duct increases to form an enlarged duct cross-section when at least a part of the distal end portion of the cannula is inserted into a body of a living subject and maintained in said body, and/or when the duct is contacted by an aqueous liquid, for a period of time sufficient for the enlarged duct cross-section to form; and
a hub having a passageway therethrough from a first to a second end thereof, said passageway having a cross-sectional area throughout at least substantially equal to the enlarged duct cross-section, said first end of said hub being attached to said proximal end portion of said cannula with said passageway through said hub in flow communication with said duct in said proximal end portion of said cannula, said attaching being in a manner such that the cross-sectional area of the duct adjacent the proximal end portion, following formation of the enlarged duct cross-section, is throughout at least substantially equal to the enlarged duct cross-section along the remainder of the cannula.

14. A catheter assembly as set forth in claim 13, wherein the increase in the duct cross-section is at least about 25%.

15. A catheter assembly as set forth in claim 13, wherein said first end (630) of said hub is integral with said proximal end portion (618) of said cannula and said duct is a continuation of said passageway, said first end of said hub having a lesser wall thickness than said second end of said hub, and said hub is formulated of a hub material selected such that an inner cross-section of the passageway increases when at least a part of the distal end portion of the cannula is inserted into a body of a living subject and maintained in said body, and/or when the passageway or the duct is contacted by an aqueous liquid, for a period of time sufficient for the enlarged duct cross-section to form.

16. A catheter assembly as set forth in claim 15, further including:
radial expansion preventing means for preventing radial expansion of said second end of said hub.

17. A catheter assembly as set forth in claim 15, wherein the material of said cannula and said hub material are each independently either:
I. a first composition comprising:
(a) first phase which comprises a substantially non-hydrophilic polymeric component, and
(b) a second phase which comprises a hydrophilic polymeric component, said first composition (i) being capable of absorbing water to an extent that it softens with a softening ratio of at least about 2:1 and/or swells with a swelling ratio of at least about 1.3:1 and (ii) when substantially completely hydrated, having an energy to break of at least about 700 N-cm/cm$^3$ and a 2.5% Secant modulus of less than about 7,000 N/cm; or
II. a second composition comprising:

a thermoplastic compound with shape-memory properties and a glass transition temperature of greater than room temperature but less than about body temperature.

18. A catheter assembly as forth in claim 13, wherein said polymeric material is a plastic.

19. A catheter assembly as set forth in claim 13, wherein said cannula has an unbroken wall.

20. A catheter assembly, comprising:
a unitary polymeric cannula having a proximal end portion, a distal end portion, and a longitudinal duct therethrough from the proximal end portion to the distal end portion the duct having an initial inner cross-section which intrinsically increases to form an enlarged duct cross-section when at least a part of the distal end portion of the cannula is inserted into a body of a living subject and maintained in said body, and/or when the duct is contacted by an aqueous liquid, for a period of time sufficient for the enlarged duct cross-section to form;
a hub having a passageway therethrough from a first to a second end thereof, said passageway having a cross-sectional area throughout at least substantially equal to 125% of the initial inner cross-section of the duct; and
attaching means for attaching said proximal end portion of said cannula to said first end of said hub with said passageway through said hub in flow communication with said duct in said proximal end portion of said cannula, said attaching being in a manner such that the cross-sectional area of the duct adjacent the proximal end portion, following formation of the enlarged duct cross-section, is throughout at least substantially equal to the cross-sectional area of the passageway.

21. A catheter assembly as set forth in claim 20, wherein the increase in the duct cross-section is from about 25% to about 200%.

22. A catheter assembly as set forth in claim 20, wherein said material of said cannula comprises:
(a) a first phase which comprises a substantially non-hydrophilic polymeric component; and
(b) a second phase which comprises a hydrophilic polymeric component;
said material (i) being capable of absorbing water to an extent that it softens with a softening ratio of at least about 2:1 and/or swells with a swelling ratio of at least about 1.3:1; and (ii) when substantially completely hydrated, having an energy to break of at least about 700 N-cm/cm$^3$ and a 2.5% Secant modulus of less than about 7,000 N/cm$^2$.

23. A catheter assembly as set forth in claim 20, wherein said material of said cannula comprises a thermoplastic compound with shape-memory properties and with a glass transition temperature of greater than room temperature but less than about body temperature.

24. A catheter assembly as set forth in claim 20, wherein said cannula is of a plastic material.

25. A catheter assembly as set forth in claim 20, wherein said cannula has an unbroken wall.

26. A catheter assembly, comprising:
a unitary polymeric cannula having a proximal end portion, a distal end portion, and a longitudinal duct therethrough from the proximal end portion to the distal end portion, the duct having an initial inner cross-section which intrinsically increases to form an enlarged duct cross-section when at least a part of the distal end portion of the cannula is inserted into a body of a living subject and maintained in said body, and/or when the duct is contacted by an aqueous liquid, for a period of time sufficient for the enlarged duct cross-section to form; and
a hub having a passageway therethrough from a first to a second end thereof, said passageway having a cross-sectional area throughout at least substantially equal to 125% of the initial inner cross-section, said first end of said hub being attached to said proximal end portion of said cannula with said passageway through said hub in flow communication with said duct in said proximal end portion of said cannula, said attaching being in a manner such that the cross-sectional area of the duct adjacent the proximal end portion, following formation of the enlarged duct cross-section, is throughout at least substantially equal to the cross-sectional area of the passageway.

27. A catheter assembly as set forth in claim 26, wherein the increase in the duct cross-section is from about 25% to about 300%.

28. A catheter assembly as set forth in claim 26, wherein said first end (630) of said hub is integral with said proximal end portion 618) of said cannula and said duct is a continuation of said passageway, said first end of said hub having a lesser wall thickness than said second end of said hub, and said passageway has an inner cross-section which increases when at least a part of the distal end portion of the cannula is inserted into a body of a living subject and maintained in said body, and/or when the passageway or the duct is contacted by an aqueous liquid, for a period of time sufficient for the enlarged duct cross-section to form.

29. A catheter assembly as set forth in claim 28, further including:
radial expansion preventing means for preventing radial expansion of said second end of said hub.

30. A catheter assembly as set forth in claim 28, wherein the cannula and the hub are each independently formulated of either:
I. a first composition comprising:
(a) first phase which comprises a substantially non-hydrophilic polymeric component, and
(b) a second phase which comprises a hydrophilic polymeric component, said first composition (i) being capable of absorbing water to an extent that it softens with a softening ratio of at least about 2:1 and/or swells with a swelling ratio of at least about 1.3:1 and (ii) when substantially completely hydrated, having an energy to break of at least about 700 N-cm/cm$^3$ and a 2.5% Secant modulus of less than about 7,000 N/cm; or
II. a second composition comprising:
a thermoplastic compound with shape-memory properties and a glass transition temperature of greater than room temperature but less than about body temperature.

31. A catheter assembly as set forth in claim 26, wherein said cannula is of a plastic material.

32. A catheter assembly as set forth in claim 26, wherein said cannula has an unbroken wall.

* * * * *